(12) United States Patent
Drapeau (10) Patent No.: US 9,504,698 B2
(45) Date of Patent: Nov. 29, 2016

(54) FLOWABLE COMPOSITION THAT SETS TO A SUBSTANTIALLY NON-FLOWABLE STATE

(75) Inventor: Susan J. Drapeau, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1007 days.

(21) Appl. No.: 12/608,300

(22) Filed: Oct. 29, 2009

(65) Prior Publication Data

US 2011/0104233 A1   May 5, 2011

(51) Int. Cl.
*A61K 31/573* (2006.01)
*A61K 9/00* (2006.01)

(52) U.S. Cl.
CPC ........... *A61K 31/573* (2013.01); *A61K 9/0024* (2013.01)

(58) Field of Classification Search
None
See application file for complete search history.

(56) References Cited

U.S. PATENT DOCUMENTS

| | | | |
|---|---|---|---|
| 5,599,552 A * | 2/1997 | Dunn et al. | 424/423 |
| 6,004,573 A | 12/1999 | Rathi et al. | |
| 6,069,129 A | 5/2000 | Sandberg et al. | |
| 6,179,862 B1 | 1/2001 | Sawhney | |
| 6,287,588 B1 | 9/2001 | Shih et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,685,957 B1 * | 2/2004 | Bezemer et al. | 424/426 |
| 6,773,714 B2 | 8/2004 | Dunn et al. | |
| 7,217,776 B1 | 5/2007 | Mallapragada et al. | |
| 2002/0009454 A1 | 1/2002 | Boone et al. | |
| 2002/0090398 A1 | 7/2002 | Dunn et al. | |
| 2004/0001872 A1* | 1/2004 | Shih et al. | 424/426 |
| 2004/0018228 A1* | 1/2004 | Fischell et al. | 424/450 |
| 2004/0072799 A1 | 4/2004 | Li et al. | |

(Continued)

FOREIGN PATENT DOCUMENTS

| | | |
|---|---|---|
| WO | 02098464 | 12/2002 |
| WO | 03005961 | 1/2003 |
| WO | WO 2008041245 A2 * | 4/2008 |

OTHER PUBLICATIONS

Saito et al., "Biodegradable poly-D,L-lactic acid-polyethylene glycol block copolymers as a BMP delivery system for inducing bone", J Bone Joint Surg Am. 2001; 83-A Suppl 1 (Pt 2):S92-8.*

(Continued)

*Primary Examiner* — Ernst V Arnold
*Assistant Examiner* — Kyung Sook Chang
(74) *Attorney, Agent, or Firm* — Sorell Lenna & Schmidt LLP (57) ABSTRACT

Flowable compositions and methods are provided for delivering a therapeutic agent at or near a target tissue site beneath the skin of a patient, the flowable composition comprising (i) a solvent, (ii) a polymer and (iii) an effective amount of the therapeutic agent, the flowable composition being capable of setting to form a substantially non-flowable composition at a physiological temperature or as the solvent contacts bodily fluid at or near the target tissue site, wherein the substantially non-flowable composition is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal.

20 Claims, 1 Drawing Sheet

(56) References Cited

U.S. PATENT DOCUMENTS

| | | |
|---|---|---|
| 2004/0082540 A1 | 4/2004 | Hermida Ochoa et al. |
| 2004/0214793 A1 | 10/2004 | Hermida Ochoa et al. |
| 2005/0142163 A1 | 6/2005 | Hunter et al. |
| 2005/0186261 A1 | 8/2005 | Avelar et al. |
| 2005/0197293 A1 | 9/2005 | Mellis et al. |
| 2006/0148903 A1 | 7/2006 | Burch et al. |
| 2006/0189944 A1 | 8/2006 | Campbell et al. |
| 2007/0116765 A1 | 5/2007 | Hu et al. |
| 2007/0156180 A1 | 7/2007 | Jaax et al. |
| 2007/0202074 A1 | 8/2007 | Shalaby |
| 2007/0243225 A1 | 10/2007 | McKay |
| 2007/0243228 A1 | 10/2007 | McKay |
| 2008/0091207 A1 | 4/2008 | Truckai et al. |
| 2008/0262216 A1 | 10/2008 | Hayakawa et al. |
| 2009/0246123 A1 | 10/2009 | Zanella et al. |

OTHER PUBLICATIONS

Atrigel Development Sheet, Jul. 2006.

* cited by examiner

FLOWABLE COMPOSITION THAT SETS TO A SUBSTANTIALLY NON-FLOWABLE STATE

BACKGROUND

Localized delivery of therapeutic agents (e.g., intrathecally, intraspinally, intraarticularly, etc.) has become increasingly more popular over the years because it has several advantages over more conventional routes of drug delivery such as oral delivery. Localized delivery has the advantage of allowing the therapeutic agent to be implanted directly at the site where drug action is needed. This becomes especially important for drugs that have unwanted systemic side effects.

Localized delivery of therapeutic agents protects the therapeutic agent from first-pass metabolism (e.g., break down due to gastric and liver enzymes) and thus improves the drug's availability in vivo at the desired target site. This particular feature makes this technology particularly attractive for the delivery of labile drugs such as proteins and peptides. Extended release formulations that can be locally delivered can also improve patient compliance. For example, therapeutic agents can be encapsulated and delivered locally allowing the drug to be released over extended periods (e.g., 6 months or longer), thereby eliminating the need for multiple injections.

In the past, localized repeat delivery of therapeutic agents has been used to treat chronic debilitating diseases such as osteoarthritis. Osteoarthritis is a chronic condition that affects millions of people in the world and is a type of arthritis that is caused by the chronic breakdown and eventual loss of cartilage in one or more joints. Osteoarthritis often affects synovial joints, such as the knees, hips, fingers, thumbs, neck, and spine. Severe forms of the disease are extremely disabling and restrict a patient's lifestyle. Localized delivery via intraarticular injection of corticosteroids, hyaluronan or hylan provide some short term relief in controlling the pain symptoms of osteoarthritis.

Sciatica, another chronic debilitating disease, can be a painful condition associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. In the past, localized delivery of corticosteroids (e.g., epidural) has been used to provide short term relief of the inflammation and pain associated with sciatica.

Newer methods are currently being investigated for treatment of chronic debilitating diseases utilizing localized delivery of drug depots. In these treatments typically the drug depot is delivered locally to the treatment site and the drug is released from the depot in a relatively uniform dose over weeks, months or even years. Localized delivery of drug depots is becoming especially important and popular in modulating the immune, inflammation and/or pain responses in treatment of chronic diseases.

Sometimes after the drug depot is implanted at the treatment site, unfortunately, the drug depot may migrate from the implant site prior to surgical closure (e.g. floats off in the blood or shifts as tissues are repositioned during surgical site closure) or as physiological conditions change (e.g., repair and regeneration of cells, tissue in growth, movement at the implant site, etc.). At times, this may reduce the efficacy of the drug as the drug depot migrates away from the implant site and lodges in a distant site. If this occurs, often the drug depot will have to be removed from the distant site and be reinserted causing additional physical and psychological trauma to a patient. In some cases, if the drug depot migrates into a joint, the drug depot may inhibit movement. In more severe cases, if the drug depot migrates into a blood vessel, it may restrict blood flow causing an ischemic event (e.g., embolism, necrosis, infarction, etc.), which could be detrimental to the patient.

In other cases there is no drug depot formulation on the market, for example epidural delivery of corticosteroids. In this case the drug is typically injected near the site of inflammation, but rapidly diffuse away from the injection site. Likewise, injection of the drug near the site of inflammation is important in achieving the best clinical outcome, but it is difficult to determine the precise location of the needle tip during injection and therefore the precise placement of the drug.

New drug depot compositions and methods are needed, which can easily allow for the accurate and precise placement of a drug with minimal physical and psychological trauma to a patient and that retain the drug at the desired target location longer. In addition, drug compositions and methods are needed that accurately and precisely allow placement of the drug depot in a manner that optimizes location, accurate spacing, and drug distribution.

SUMMARY

New drug compositions and methods are provided, which can easily allow accurate and precise implantation of a drug in situ with minimal physical trauma to the injection site tissue. One advantage of the compositions and methods of the invention is that the drug can now be easily delivered to the target tissue site (e.g., synovial joint, at or near the spinal column, etc.) using a viscous yet flowable composition (e.g., a liquid, gel, suspension, etc.) that does not harden upon contact with the target tissue, but which increases in viscosity to a substantially non-flowable state. In this way, accurate and precise implantation of a drug in a minimally invasive procedure can be accomplished and the drug can be held in a relatively confined space without damaging the surrounding tissue. In some embodiments, the composition reacts with the physiological fluids of the patient to produce a denser exterior surface or film on the viscous carrier composition, thereby rendering the composition substantially non-flowable. Thus, the therapeutic agent can be confined within the substantially non-flowable composition, or flexible drug depot, and released over a period of at least one day, at least one week, at least two weeks or at least one month.

In exemplary embodiments, a flowable composition is provided for delivering a therapeutic agent at or near a target tissue site beneath the skin of a patient, the flowable composition comprising (i) solvent, (ii) a polymer and (iii) an effective amount of the therapeutic agent, the flowable composition remaining substantially viscous at physiological temperature or wherein the solvent substantially increases in viscosity in response to contact with bodily fluid at or near the target tissue site to produce a substantially non-flowable composition, wherein the substantially non-flowable composition is capable of releasing the therapeutic agent over a period of at least one day, at least one week, at least two weeks or at least one month. In other exemplary embodiments, a flowable composition is provided for delivering a therapeutic agent at or near a target tissue site beneath the skin of a patient, the flowable composition comprising (i) a solvent, (ii) a contrast agent, (iii) a polymer and (iv) an effective amount of a therapeutic agent, the flowable composition increasing in viscosity in response to contact with bodily fluid at or near the target tissue site to produce a substantially non-flowable composition, wherein the substantially non-flowable composition is capable of releasing the therapeutic agent over a period of at least one day, at least one week, at least two weeks or at least one month.

In yet other exemplary embodiments, a composition is provided for delivering a therapeutic agent at or near a target tissue site beneath the skin of a patient, the composition comprising an effective amount of a therapeutic agent disposed within the composition, wherein composition is capable of developing a denser surface film when the composition comes in contact with physiological fluid at or near the target tissue site to produce a substantially non-flowable composition, but flexible composition, wherein the substantially non-flowable composition is capable of releasing the therapeutic agent over a period of at least one day, at least one week, at least two weeks or at least one month.

In some embodiments, a kit is provided for administering the drug at or near a target tissue site beneath the skin of a patient, the kit comprising (i) a flowable composition according to the invention comprising an effective amount of a therapeutic agent, the flowable composition capable of transforming to a substantially non-flowable state in response to physiological solutions, wherein the substantially non-flowable composition remains substantially separated from the physiological fluid at or near the target tissue site; and a syringe, cartridge or ampule containing the flowable composition.

In some embodiments, a method is provided for delivering a therapeutic agent into a target tissue site beneath the skin, the method comprising inserting a cannula and/or needle at or near a target tissue site and injecting a flowable composition comprising (i) a solvent, (ii) a polymer and (iii) an effective amount of the therapeutic agent, the flowable composition being capable of increasing its viscosity in response to physiological fluid at the target site to produce a substantially non-flowable composition, wherein the drug is released over a period of at least one day, at least one week, at least two weeks or at least one month, and the target tissue site comprises at least one muscle, ligament, tendon, cartilage, spinal disc, spinal foraminal space near the spinal nerve root, facet or synovial joint, or spinal canal.

In other exemplary embodiments, a method is provided for delivering a therapeutic agent into a target tissue site beneath the skin, the method comprising inserting a cannula and/or needle at or near a target tissue site and injecting a flowable composition comprising (i) a solvent, (ii) a polymer and (iii) an effective amount of an anti-inflammatory therapeutic agent, the flowable composition being capable of increasing its viscosity or developing a denser surface film to form a substantially non-flowable composition comprising a slowly degradable carrier and a corticoid steroid therein, wherein the composition is flowable below a physiological temperature or before the solvent contacts bodily fluid at or near the target tissue site, wherein the physiological temperature or contact with bodily fluid causes the composition to assume a substantially non-flowable state that is capable of releasing the therapeutic agent over a period of at least one day, at least one week, at least two weeks or at least one month. For example, the flowable composition may develop a denser surface film when the composition comes in contact with physiological fluid to produce a flexible drug depot and/or the flowable composition may substantially increase in viscosity when the composition comes in contact with physiological fluid to produce a flexible drug depot.

In yet other exemplary embodiments, a method is provided comprising administering a therapeutic agent in a biocompatible polymeric material beneath the skin of a subject. The therapeutic agent is soluble both in water and in alcohol and the biocompatible polymeric material is a liquid methacrylate copolymer such as an ammonium methacrylate copolymer and an ammonium methacrylate copolymer or a mixture thereof (e.g., WO 02/098464). The polymers are provided in an alcoholic solution, (for example, about 96 percent), or alcohol-water solution (e.g., 80:20 w/w), wherein the alcohol dissipates in the biological fluids within the subject causing the polymer to form a polymeric film within the subject and wherein the therapeutic agent is trapped within the polymeric film and slowly released from the polymeric film. The release rate may be adjusted by manipulating the ratio of the two polymeric materials. In yet another exemplary embodiment, the solvent is a polymer having a gelation temperature at or below the body temperature of the subject to be treated, e.g., 98° F., such that upon injection of the composition it sets into a gel entrapping the therapeutic agent within it, for example, when injected into the muscle, tendons and/or ligaments surrounding the spine. In an exemplary embodiment, the therapeutic agent is a corticosteroid (see U.S. Pat. No. 6,004,573).

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the invention, and thus, some features may be exaggerated in order to illustrate a specific feature of the invention.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the scope of the invention are approximations, the numerical values set forth herein are reported as precisely as possible. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a therapeutic agent" includes one, two, three or more therapeutic agents.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug compositions and methods are provided, which can easily allow accurate and precise implantation of a drug with minimal degradation and disolution. The drug compositions and methods provided utilize a flowable composition (e.g., gel, suspension, solution) that substantially increases in viscosity or develops a denser surface film on contact with the target tissue site. Optionally, the composition may comprise one or more contrast agents. In this way, accurate and precise implantation of a drug depot in a minimally invasive procedure can be accomplished. In various embodiments, the flowable composition avoids mechanical disruption of the target site reducing physical trauma to the injection site and patient. In various embodiments, the flowable composition allows accurate placement of the depot in a manner to optimize location, accurate spacing, and drug distribution by incorporating one or more contrast agents that allow for accurate medical imaging during the injection procedure.

In some embodiments, a flowable composition is provided for delivering a therapeutic agent at or near a target tissue site beneath the skin of a patient, the flowable composition comprising (i) a solvent and (ii) an effective amount of the therapeutic agent, the flowable composition being capable of substantially increasing in viscosity or developing a denser surface film to form a flexible drug depot at a physiological temperature or as the solvent contacts bodily fluid at or near the target tissue site.

Flowable compositions include liquid (e.g., solution, suspension, or the like) or semi-solid compositions (e.g., gels) that are easy to manipulate and may be injected at or near the target tissue site and that substantially increase in viscosity or develop a denser surface film at or near the injection site to entrap the therapeutic agent in a now substantially non-flowable composition and delay dissolution of the therapeutic agent.

As used herein, "flowable" means a formulation with a viscosity low enough that the composition can be injected through a 16 gauge or smaller needle and that increases in viscosity.

As used herein, "biocompatible" means a property or characteristic of a viscous vehicle to disintegrate or break down, over a prolonged period of time, in response to the biological environment in the patient, by one or more physical or chemical degradative processes, for example by enzymatic action, oxidation or reduction, hydrolysis (proteolysis), displacement, e.g. ion exchange, or dissolution by solubilization, emulsion or micelle formation, and which material is then absorbed by the body and surrounding tissue, or otherwise dissipated thereby.

As used herein, "drug" or "therapeutic agent" means any substance that alters the physiology of the patient. The terms "drug" and "therapeutic agent" may be used interchangeably herein and should be understood to mean a therapeutically effective amount of the drug or therapeutic agent. It will be understood that a "drug" or "therapeutic agent" includes more than one therapeutic agent, for example, a combination of two or more drugs.

As used herein, a "therapeutically effective amount" or an "effective amount" is and amount of the drug or therapeutic agent such that when administered, the drug results in alteration of the biological activity, such as, for example, inhibition of inflammation, reduction or alleviation of pain, improvement in a condition, etc. The dosage administered to a patient can be as a single dose or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

As used herein, "cure" or "set" mean the transition from a flowable state to a substantially non-flowable state.

As used herein, a "substantially non-flowable state" means an increase in viscosity such that the composition can no longer be injected through a 16 gauge needle under a pressure of less than about 750 N or less than about 450 N.

As used herein, "biocompatible" means that the flowable composition will degrade or be absorbed over time in the body and that neither the depot and/or flowable composition will cause substantial tissue irritation or necrosis at the target tissue site. In various embodiments, "biocompatible" means that the flowable composition can break down or degrade within the body to non-toxic components after or while a therapeutic agent has been or is being released.

In various embodiments, the flowability of the formulation allows it to conform to irregularities, crevices, cracks, and/or voids in the tissue site. In the present applications, a therapeutic agent is added to the flowable composition so that when the flowable composition increases in viscosity or develops a denser surface film to transform the composition from a flowable composition to a substantially non-flowable composition inside the body, the therapeutic agent is then released in a sustained manner through the polymer matrix by direct dissolution, degradation and/or erosion of the polymer matrix.

In various exemplary embodiments, the composition provides an optimal drug concentration at a distance of up to about 1 mm, or to about 5 cm, from the implant site.

Examples of therapeutic agents include, those that are direct- and local-acting modulators of pro-inflammatory cytokines, such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Other therapeutic agents can include extracellular matrix proteins that may be critical to the repair of a target tissue. An example would be MIA/CD-RAP (melanoma inhibitory activity/cartilage-derived retinoic-acid-sensitive protein), which is a matrix component for mature and developing cartilage.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine[2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Specific examples of corticoid steroids includes, but is not limited to, Hydrocortisone, Hydrocortisone acetate, Cortisone acetate, Tixocortol pivalate, Prednisolone, Methylprednisolone, Prednisone, Triamcinolone acetonide, Triamcinolone alcohol, Mometasone, Amcinonide, Budesonide, Desonide, Fluocinonide, Fluocinolone acetonide, Halcinonide, Betamethasone, Betamethasone sodium phosphate, Dexamethasone, Dexamethasone sodium phosphate, Fluocortolone, Hydrocortisone-17-butyrate, Hydrocortisone-17-valerate, Aclometasone dipropionate, Betamethasone valerate, Betamethasone dipropionate, Prednicarbate, Clobetasone-17-butyrate, Clobetasol-17-propionate, Fluocortolone caproate, Fluocortolone pivalate, Fluprednidene acetate, and combinations thereof.

Suitable anabolic growth or anti-catabolic growth factors include, but are not limited to, a bone morphogenetic protein, a growth differentiation factor (GDF), a LIM mineralization protein, CDMP or progenitor cells or a combination thereof. Examples include, but are not limited to, BMP-2, rhBMP-2, BMP-3, rhBMP-3, BMP-4 (also referred to as BMP-2B), rhBMP4 (also referred to as rhBMP-2B), BMP-5, rhBMP-5, BMP-6, rhBMP-6, BMP-7 (OP-1), rhBMP-7 (rhOP-1), BMP-8, rhBMP-8, BMP-9, rhBMP-9, BMP-12, rhBMP-12, BMP-13, rhBMP-13, BMP-15, rhBMP-15, BMP-16, rhBMP-16, BMP-17, rhBMP-17, BMP-18, rhBMP-18, GDF-1, rhGDF-1, GDF-3, rhGDF-3, GDF-5, rhGDF-5, GDF-6, rhGDF-6, GDF-7, rhGDF-7, GDF-8, rhGDF-8, GDF-9, rhGDF-9, GDF-10, rhGDF-10, GDF-11, rhGDF-11, GDF-12, rhGDF-12, GDF-14, and rhGDF-14.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The compositions of the present invention may also contain other non-active ingredients. Other non-active ingredients may have multiple purposes, including, but not limited to, carrying, stabilizing and/or controlling the release of the therapeutic agent(s). The controlled release process, for example, may be by a solution-diffusion mechanism or it may be governed by an erosion-controlled process.

Typically, after the flowable composition increases in viscosity to a non-flowable state or develops a denser surface film to produce a substantially non-flowable composition, i.e., transforming into a flexible drug depot, the flexible drug depot will be in a gelatenous or semi-solid state and will be a biocompatible material.

Typically, the composition cures or sets to a substantially non-flowable state in from about 0.1 minutes to 2 hours, or from about 1 minute to about 1 hour, or from about 2 minutes to 30 minutes, or from about 1 minute to about 30 minutes.

In various embodiments, the formulation may have a therapeutic agent comprising about 0.01-90 wt % of the depot, or 0.1-60 wt % of the depot, or 1-30 wt % of the depot. The balance being the solvent or carrier material and any optional inactive materials.

In many instance, it may be desirable to formulate the carrier or solvent material from a biodegradable material. There are numerous materials available for this purpose and having the characteristic of being able to breakdown or disintegrate over time. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

Suitable materials for the solvent or carrier are ideally pharmaceutically acceptable biodegradable and/or any bioabsorbable materials (biocompatible materials), which may be FDA approved or GRAS materials. These biocompatible materials may also be polymeric or non-polymeric, as well as synthetic or naturally occurring, or a combination thereof.

In various embodiments, the flowable composition comprises poly (lactide-co-glycolide) (PLGA) and polyethylene glycol (PEG) conjugates (see U.S. Pat. No. 6,004,573), polyisopropylacrylamide and polyacrylic acid conjugates (see US Patent Pub. 2007/0116765), methacrylic copolymers (see U.S. Pat. No. 7,217,776), PEG-PLGA-PEG triblock copolymers, polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, SAIB (sucrose acetate isobutyrate) or combinations thereof.

The composition may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %.

Radiographic markers can be included in the flowable composition to permit the user to accurately position the composition into the target site of the patient. These radiographic markers will also permit the user to track movement and degradation of the substantially non-flowable composition over time. In this embodiment, the user may accurately position the flowable composition in the site using any of the numerous diagnostic imaging procedures. Such diagnostic imaging procedures include, for example, X-ray imaging, MRI, or fluoroscopy. Examples of such radiographic markers include, but are not limited to, barium, calcium, and/or metal beads or particles.

Generally, the biocompatible, biodegradable branched thermoplastic polymer is substantially soluble in the organic solvents so that up to 50-60 wt % solids can be made. In some embodiments, the polymers can be soluble in the organic solvent so that mixtures up to 85-98 wt % solids can be made. In some embodiments, the polymers can be insoluble in water so that less than 0.1 g of polymer per mL of water will dissolve or disperse in water. In some embodiments, the polymers used can be insoluble in water so that less than 0.001 g of polymer per mL of water will dissolve or disperse in water. At this level, the flowable composition with a completely water miscible solvent will almost immediately (e.g., within 30 minutes or less) transform to substantially non-flowable state.

Solvents suitable for use in the flowable composition are biocompatible and are at least slightly soluble in bodily fluids, tissue fluids or water. In some embodiments, the organic solvent is moderately soluble or very soluble at all concentrations in bodily fluids, tissue fluids or water. A solvent that is at least slightly soluble in bodily fluids or tissue fluids to allow water to permeate into the polymer solution over a period of time ranging from seconds to hours and cause it to coagulate into a substantially non-flowable state. Moderately soluble to very soluble solvents will diffuse from the flowable composition over a period of seconds to hours so that the transformation will occur rapidly but with sufficient leisure to allow its injection and sufficient spreading. The organic solvent includes a polar aprotic or polar protic organic solvent. In some embodiments, the organic solvent may have a molecular weight in the range of about 30 to about 1000.

In some embodiments, it is believed that the transition of the flowable composition to a substantially non-flowable state is the result of the dissipation of the organic solvent from the flowable composition into the surrounding aqueous medium or body fluid and the infusion of water from the surrounding aqueous medium or body fluid into the organic solvent within the flowable composition.

Examples of biocompatible organic solvents that may be used to form the flowable compositions include aliphatic, aryl, and arylalkyl linear, cyclic and branched organic compounds that are liquid or at least flowable at ambient and physiological temperature and contain such functional groups as alcohols, ketones, ethers, amides, esters, carbonates, sulfoxides, sulfones, and any other functional group that is compatible with living tissue.

In some embodiments, biocompatible organic solvents that are at least slightly soluble in aqueous or body fluid include N-methyl-2-pyrrolidone, 2-pyrrolidone; C1 to C15 alcohols, diols, triols and tetraols such as ethanol, glycerine, propylene glycol, butanol; C3 to C15 alkyl ketones such as acetone, diethyl ketone or methyl ethyl ketone; C3 to C15 esters such as methyl acetate, ethyl acetate, ethyl lactate; C1 to C15 amides such as dimethylformamide, dimethylacetamide or caprolactam; C3 to C20 ethers such as tetrahydrofuran, or solketal; tweens, triacetin, propylene carbonate, decylmethylsulfoxide, dimethyl sulfoxide, oleic acid, or 1-dodecylazacycloheptan-2-one. Other solvents include, for example, benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, dimethyl sulfoxide, triacetin, propylene carbonate or triethyl citrate. Exemplary solvents include dimethyl sulfoxide, triacetin, or propylene.

The solubility of the polymers in the various solvents will differ depending upon their crystallinity, their hydrophilicity, hydrogen-bonding, and molecular weight. Lower molecular-weight polymers will normally dissolve more readily in the solvents than high-molecular-weight polymers. As a result, the concentration of a polymer dissolved in the various solvents will differ depending upon type of polymer and its molecular weight. Moreover, the higher molecular-weight polymers will tend to give higher solution viscosities than the low-molecular-weight materials.

Generally, the concentration of the polymer in the solvent can range from about 0.01 g per ml of solvent to a saturated concentration. Typically, the saturated concentration will be in the range of 80 to 95 wt % solids or 4 to almost 5 gm per ml of solvent assuming that the solvent weighs approximately 1 gm per ml.

For polymers that tend to coagulate slowly, a solvent mixture can be used to increase the coagulation rate. For example, one liquid component of the solvent mixture is a good solvent for the polymer, and the other liquid component of the solvent mixture is a poorer solvent or a non-solvent. The two liquids are mixed at a ratio such that the polymer is still soluble but precipitates with the increase in the amount of poorer solvent. Thus, the solvent system can be miscible with both the polymer and water. An example of such a binary solvent system is the use of N-methylpyrrolidone and ethanol. The addition of ethanol to the NMP/polymer solution increases its coagulation rate.

In other exemplary embodiments addition of an initiator/activator to enhance setting the setting time may also be added.

The flowable composition may optionally have one or more emulsifying agents. Examples of emulsifying agents include, but are not limited to, water, ethanol, other alcohols, polyols, esters, carboxylic acids, ketones, aldehydes, propylene glycol, ethylene glycol, glycerol, and solutions and mixtures thereof.

The proportions of flowable composition can range as follows, expressed as a percentage of the total weight of the composition prior to administration to a subject: Polymer
about 5% to about 90%
Solvent about 15% to about 95%
Emulsifying about 0% to about 80%
Pharmaceutical agent about 0.1% to about 50%
Diluents about 0% to about 40%

If the therapeutic agent is hydrophilic, then one may want to use polar solvents (albeit a polar solvent that is not toxic to the subject in the levels used). Polar solvents should be somewhat water soluble, having a Hildebrand Solubility Parameter of at least about 7.5 or 8 $(cal/cc)^{1/2}$, usually at least about 9 $(cal/cc)^{1/2}$, and often times, 10 $(cal/cc)^{1/2}$.

In some embodiments, the polymer can be thermosetting, e.g., it changes from a liquid at room temperature to a gel at body temperature when the liquid reaches a pre-determined temperature. The sol-to-gel transition temperature can be above room temperature (e.g., 64.4° F.-75.2° F.) to body temperature (e.g., 96° F.-105° F.).

Thermosetting compositions that may be used in the invention typically involve a mixture of polymers that form a block copolymer having hydrophobic segments and hydrophilic segments. A block copolymer can be a tripolymer of hydrophobic-hydrophilic-hydrophobic segments or hydrophilic-hydrophobic-hydrophilic segments. Alternatively, the block copolymer can be a repeating hydrophobic-hydrophilic or hydrophilic-hydrophobic segments with one additional segment.

The hydrophobic polymers can include, but are limited to, poly(D,L-lactic acid), poly(L-lactic acid), poly(D-lactic acid), poly(D,L-lactic-co-glycolic acid), poly(L-lactic-co-glycolic acid), poly(ε-caprolactone), poly(γ-butyrolactone), poly(δ-valerolactone), poly(ε-caprolactone-co-lactic acid), poly(c-caprolactone-co-glycolic acid-co-lactic acid), hydroxybutyric acid, malic acid, and bi- or terpolymers thereof. Another hydrophobic polymer can be poly(ethylene carbonate). In some embodiments the average molecular weight of the hydrophobic polymer blocks are less than 100,000. The average molecular in other embodiments can range from about 1,000 to about 3,000 or from about 1,000 to about 10,000.

The hydrophilic polymer can include, but is not limited to, polyethylene glycol, and polyethylene oxides. In some embodiments, the above molecular weight of the hydrophilic polymer blocks are between 300 and 20,000. In other embodiments, the average molecular weight is between about 500 and 10,000.

Other examples of thermosetting depots can contain block polymers of polyethylene oxides (as known as polyoxyethylene or PEO) and poly-propylene oxide (also known as polyoxypropylene or PPO) (PEO-PPO-PEO, Pluronics®, BASF, Florham Park, N.J.); block polymers of polyethylene oxides, poly-propylene oxide, and poly(aspartic acid) (PEO- PPO-PAA); and poly(lactide-co-glycolide) or block polymers of polyethylene oxides (PLGA-PEO-PLGA).

The amount of polymer in the flowable composition can range from about 1% to about 99% by weight, the pharmaceutical agent can range from about 0.01% to about 50% by weight, and the diluents can range from 0% to about 60% by weight.

In various embodiments, the flowable composition may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, gellan gum, albumin, fibrin, vitamin E analogs, such as alpha tocopheryl acetate, d-alpha tocopheryl succinate, D,L-lactide, or L-lactide,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the composition in a controlled and/or sustained manner. For example, the flowable composition containing the therapeutic agent and a polymer matrix can be injected at the target tissue site and the polymer matrix breaks down over time (e.g., days, months) within the target tissue site releasing the therapeutic agent. The composition is capable of carrying at least one pharmaceutical agent in quantities sufficient for therapeutic or prophylactic treatment over a pre-selected period of time. The depot can release the therapeutic agent over 1 day, over 2 days, over 3 days, over 4 days, over 5 days, over 10 days, over 15 days, over 20 days, or over 30 days. In an alternative embodiment, the composition can release the therapeutic agent over 30 days, over 60 days, over 90 days, over 180 days, over 6 months, over 9 months, over 12 months, over 14 months, over 16 months, and over 18 months. In another embodiment, the composition can contain two or more therapeutic agents, each one being released over different number of days or months.

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the substantially non-flowable composition or as the result of metabolic transformation or dissolution of the therapeutic agent(s) or conjugates of therapeutic agent (s).

In various embodiments, the flowable composition can be designed to cause an initial burst dose of therapeutic agent within the first 24 hours after implantation. "Initial burst" or "burst effect" or "bolus dose" refers to the release of therapeutic agent from the flowable composition during the first 24 hours after the flowable composition comes in contact with an aqueous fluid (e.g., synovial fluid, cerebral spinal fluid, etc.). The "burst effect" could be due to the increased release of therapeutic agent from the flowable composition while it is coagulating, developing a denser surface film or increasing viscosity to form a substantially non-flowable implant. In alternative embodiments, the flowable composition is designed to avoid this initial burst effect.

In various embodiments, the flowable composition has a pre-dosed viscosity in the range of about 1 to about 500 centipoise (cps), 1 to about 200 cps, or 1 to about 100 cps. After the flowable composition is administered to the target site, the viscosity of the flowable composition will increase and the flowable composition will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the flowable composition has an inherent viscosity (abbreviated as "I.V." and units are in deciliters/gram), which is a measure of the flowable composition's molecular weight and degradation time (e.g., a flowable composition with a high inherent viscosity has a higher molecular weight and longer degradation time). Typically, a flowable composition with a high molecular weight provides a stronger matrix and the matrix takes more time to degrade. In contrast, a flowable composition with a low molecular weight degrades more quickly and provides a softer matrix. In various embodiments, the flowable composition has a molecular weight, as shown by the inherent viscosity, from about 0.10 dL/g to about 1.2 dL/g or from about 0.10 dL/g to about 0.40 dL/g.

In one exemplary embodiment, the flowable composition is a gel for delivering a therapeutic agent to a target tissue site beneath the skin of a patient. The gel being capable of developing a denser surface film at the target tissue site, wherein the target tissue site comprises at least one muscle, ligament, tendon, cartilage, spinal disc, spinal foraminal space near the spinal nerve root, facet or synovial joint, or spinal canal.

In various embodiments, the flowable composition can have a viscosity of from about 5 to about 300 cps, from about 10 cps to about 50 cps, from about 15 cps to about 75 cps at room temperature, which allows it to be injected at or near the target site. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly(hydroxyethylmethacrylate), poly (methoxyethylmethacrylate), poly(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the flowable material has the ability to either respond rapidly to mechanical motion by stretching or does not adhere to the tissue, thereby allowing muscles to move over and by the substantially non-flowable composition when in the human body.

In various embodiments, the therapeutic agent may be contained within microspheres within the polymer. In one embodiment, the microspheres provide for a sustained release of the therapeutic agent. In yet another embodiment, the polymer, which is biodegradable, prevents the microspheres from releasing the therapeutic agent; the microspheres thus do not release the therapeutic agent until they have been released from the polymer.

It will be appreciated by those with skill in the art that the flowable composition can be administered to the target site using a cannula or needle that can be a part of a drug delivery device e.g., a syringe, a gun drug delivery device, or any medical device suitable for the application of a drug to a targeted organ or anatomic region. The cannula or needle to be used with the invention is designed to cause minimal physical and psychological trauma to the patient.

In various embodiments, one or more components of the flowable composition are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, leaves no residues and does not have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the flowable composition, including, but not limited to, gas sterilization, such as, for example, with ethylene oxide or steam sterilization.

In various embodiments, a kit is provided which may include additional parts along with the flowable composition combined together to be used to implant the flowable composition. The kit may include in a first compartment an ampule, cartridge or syringe holding the flowable composition to be injected at the target site, and any other instruments needed for the localized drug delivery. A second compartment may include gloves, drapes, and other procedural supplies for maintaining sterility of the implanting process, as well as an instruction booklet. Each item may be packaged together or separately in a plastic pouch that is radiation sterilized. A cover of the kit may include illustrations of the intended procedure and a clear plastic cover may be placed over the compartments to maintain sterility.

In various embodiments, when the target site comprises a joint or spinal region, a portion of fluid (e.g., synovial fluid, spinal fluid, etc.) can be withdrawn from the target site through the cannula or needle first and then the flowable composition administered (e.g., injected) to the target site. The target site will re-hydrate (e.g., replenishment of fluid) and this aqueous environment will provide a suitable aqueous environment for the setting or curing of the flowable composition. In addition, the composition may retain hydration to maintain physiologically friendly environment for a period of time and/or to lubricate the contact area between the substantially non-flowable implant and the surrounding tissue.

The flowable composition may be used for localized delivery of the therapeutic agent to the patient to treat a disease or condition such as for example, osteoarthritis, rheumatoid arthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, or the like. In various embodiments, the flowable composition may also be used to repair tissue as well deliver a therapeutic agent.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of the flowable composition at or near the target site as needed for treatment of pain, inflammation or other disease or condition.

In various embodiments, the flowable composition may be used to treat rheumatoid arthritis (RA) and/or osteoarthritis by inserting a cannula at or near a target tissue site and injecting the flowable composition at the target site and allowing it to set into a substantially non-flowable state.

RA is a chronic systemic disease characterized by progressive joint deformity and joint destruction in which cytokines play a central pathogenic role. The clinical course of RA is variable and often shows a remitting pattern. Three forms of RA can be distinguished: mild, self-limiting disease; mildly progressive disease; and aggressive disease, which is difficult to control with medication, and is characterized by functional decline and radiologic deterioration of the joints, e.g., joint space narrowing and erosions. In accordance with the systemic nature of RA, there are extra-articular manifestations, which include vasculitis, alveolitis, and ocular disease. Onset of RA is often insidious with fatigue, anorexia, generalized weakness, and vague musculoskeletal symptoms. Specific symptoms appear later. Several joints, usually in a symmetrical fashion, are affected. Most often these are joints of the hands, wrists, knees, and feet. Joints are painful and swollen, and motion is limited. With persistent inflammation, a variety of deformities develop which include most typically radial deviation of the wrist and hyperextension or flexion of the proximal interphalangeal joints; other deformities occur as well. Atrophy of skeletal muscle sets in. In approximately 20 to 30% of all patients, there is development of rheumatoid nodules on periarticular structures or sites of trauma, but they are usually of limited clinical significance. The nodules may be found in other structures such as the pleura or the meninges. Laboratory findings may include elevation of erythrocyte sedimentation rate (ESR) and C-reactive protein (CRP) along with rheumatoid factor. Rheumatoid factor is an autoantibody against the Fc portion of IgG found in more than two-thirds of all patients. High titers of rheumatoid factor are a good indicator of disease activity. Mild anemia (normochromic, normocytic) and eosinophilia may be present as well. With progression of the disease, X-ray abnormalities such as general deformity, juxta-articular osteopenia, loss of articular cartilage, and bone erosion become more evident.

In one exemplary embodiment, the flowable composition is utilized to treat rheumatoid arthritis (RA) and/or osteoarthritis (OA), which is the most common form of arthritis in Western populations. Knee OA, characterized clinically by pain and functional disability, is the leading cause of chronic disability among the elderly in the US. Risk factors for arthritis include age, gender, race, trauma, repetitive stress/joint overload, muscle weakness, and genetic factors. Pathologically, the most striking changes in arthritis are the loss of articular cartilage.

In another exemplary embodiment, the flowable composition is utilized to treat the temporomandibular joint and head and neck pain associated with problems in the temporomandibular joint. In another exemplary embodiment, the flowable composition is utilized to treat facet joints and neck and/or back pain associated therewith.

Figure 1:
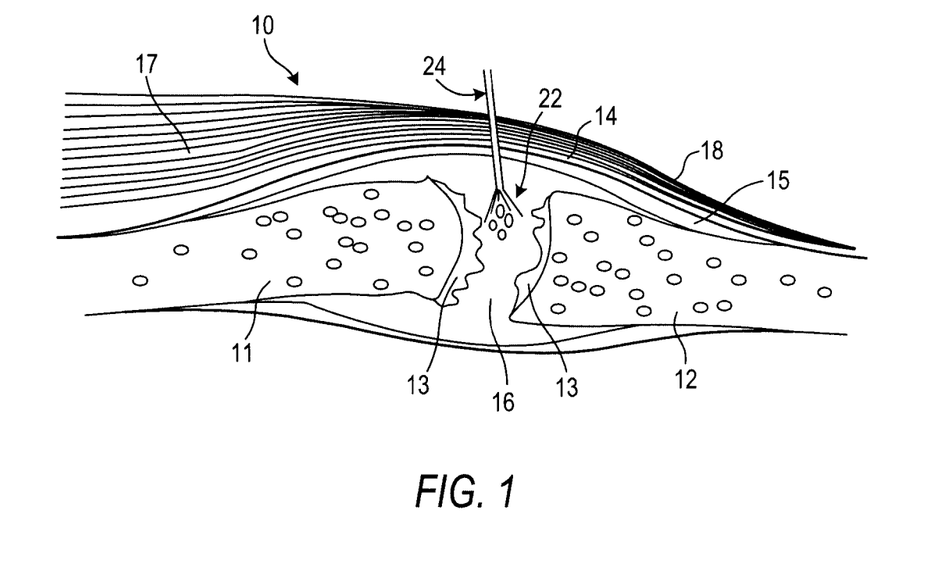
FIG. 1 illustrates a side sectional view of a joint affected by osteoarthritis and delivery of an embodiment of a flowable composition containing a therapeutic agent dispersed therein that can be administered into the synovial joint via a cannula or needle.

FIG. 1 illustrates one embodiment of the effect of osteoarthritis on the joint 10. Osteoarthritis causes the cartilage 13 to become worn away from the ends of the bones 11, 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11, 12 stable and allow the joint 10 to bend and move. However, symptoms become worse and debilitating as the disease progresses. To treat the diseased joint, the flowable composition 22 can be administered locally at the target site utilizing a cannula or needle 24 that penetrates beneath the skin to the target site 22. In this embodiment, the flowable composition is injected at the target site (shown at or near the osteolytic lesions). It will be understood that some synovial fluid 16 may be withdrawn from the joint 10 and the flowable composition added before, during, or after the synovial fluid is withdrawn. The flowable composition may also be placed at other target sites (e.g., by the meniscus or cartilage surface) and the drug released. In this way, accurate and precise implantation of a drug depot in a minimally invasive procedure can be accomplished. In various embodiments, the flowable composition avoids the need to ensure that any inserted material does not increase frictional agitation.

Figure 2:
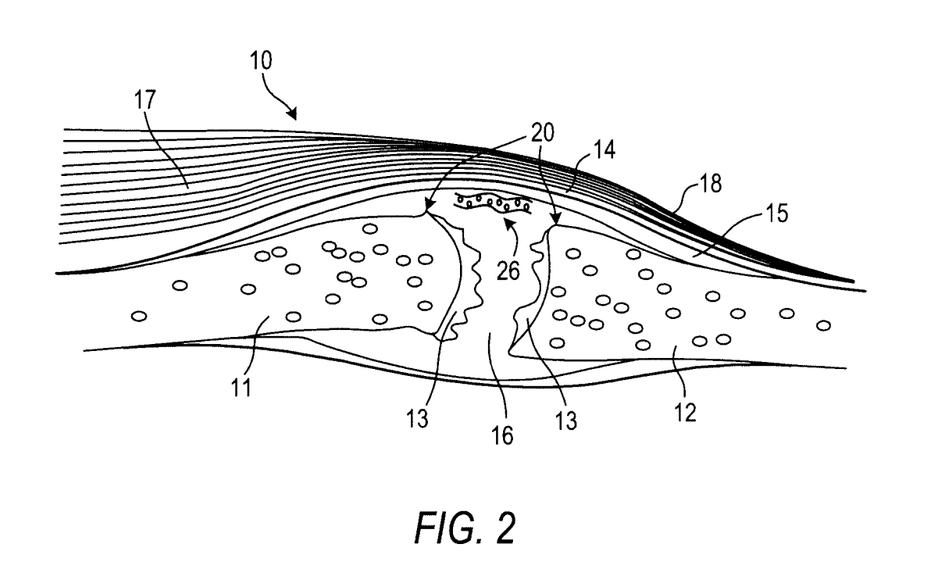
FIG. 2 illustrates a side sectional view of a joint affected by osteoarthritis and delivery of an embodiment of a flowable composition containing a therapeutic agent dispersed therein, which increases in viscosity to form a flexible drug depot after it is injected into the target tissue, in this case, a synovial joint.

FIG. 2 illustrates one embodiment of the effect of osteoarthritis on the joint 10. Osteoarthritis causes the cartilage 13 to become worn away from the ends of the bones 11 and 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11 and 12 stable and allow the joint 10 to bend and move. However, symptoms become worse and debilitating as the disease progresses. To treat the diseased joint, the flowable composition can be administered locally at the target site utilizing a cannula or needle that penetrates beneath the skin to the target site. In this embodiment, the flowable composition comprises a therapeutic agent suspended in it and the flowable composition is injected into the target site (shown near the osteolytic lesions). In this embodiment, the flowable composition has anti-adhering characteristics 26 and sets into the substantially non-flowable composition in an area that does not interfere with movement of the joint and is away from the articular surfaces of the joint.

In some embodiments, prior to administering the flowable composition, one can suction out the synovial fluid and then wash the joint with a saline solution or other physiologically neutral solution. The suctioning of fluids and addition of the physiologically neutral solution can be repeated any number of times for any length of time. The steps can occur simultaneously or as distinctly different steps. Not wishing to be bound to a particular hypothesis, it is believed that the synovial fluid of an inflamed joint contains a myriad of pro-inflammatory cytokines and other pro-inflammatory molecules. Washing out the inflamed joint removes most or all of these pro-inflammatory cytokines and other pro-inflammatory molecules and benefits the treatment regimens.

Although the joint site is shown, as described above, the flowable composition can be used to deliver a drug to any site beneath the skin, including, but not limited to, at least one muscle, ligament, tendon, cartilage, synovial joint, spinal disc, spinal foraminal space, near the spinal nerve root, facet joint, or spinal canal.

In an exemplary embodiment, the flowable composition does not interfere with the movement of the connective tissue around the site of injection.

In another exemplary embodiment, the flowable composition is deployed around a targeted tissue site (e.g., a nerve root) and sets around the targeted tissue. The flowable composition keeps the therapeutic agent closely bound to target site (e.g., a nerve root) providing a therapeutically effective dosage of the therapeutic agent to the target site, with the dosage gradient rapidly falling off outside of the region of the then substantially non-flowable composition. The therapeutic agent is therefore tightly targeted to the desired tissue site.

Having now generally described the invention, the same may be more readily understood through the following reference to the following examples, which are provided by way of illustration and are not intended to limit the present invention unless specified.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A flowable composition for delivering a therapeutic agent at or near a target tissue site beneath the skin of a patient, the flowable composition comprising (i) a solvent in an amount of about 15 wt. % of the composition, the solvent comprising an alcoholic solution (ii) a polymer comprising repeating hydrophobic-hydrophilic polymer segments, wherein the hydrophobic polymer segments are selected from a group consisting of poly(D,L-lactic acid), poly(L-lactic acid), poly(D-lactic acid), poly(γ-butyrolactone), poly(ε-caprolactone-co-lactic acid), poly(ε-caprolactone-co-glycolic acid-co-lactic acid), hydroxybutyric acid, malic acid and poly(ethylene carbonate), and (iii) an effective amount of a therapeutic agent comprising from 1 to 30 wt %, the flowable composition being capable of increasing viscosity or developing a denser surface film to form a substantially non-flowable composition at a physiological temperature or as the solvent contacts bodily fluid at or near the target tissue site, wherein the flowable composition is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal, wherein the solvent has a Hildebrand Solubility Parameter of at least about 7.5 or 8 $(cal/cc)^{1/2}$ and the flowable composition comprises a modulus of elasticity of $2\times10^4$ to about $5\times10^5$ dynes/cm$^2$, a predosed viscosity in the range of about 1 to about 200 cps and an inherent viscosity from about 0.10 dL/g to about 1.2 dL/g.

2. A flowable composition according to claim 1, wherein the flowable composition develops a denser surface film to form the substantially non-flowable composition.

3. A flowable composition according to claim 1, wherein the flowable composition comprises a solvent that diffuses away as the flowable composition sets to form the substantially non-flowable composition.

4. A flowable composition according to claim 1, wherein the flowable composition is a liquid at room temperature and increases viscosity at physiological temperature to form the substantially non-flowable composition.

5. A flowable composition according to claim 1, wherein the therapeutic agent comprises an anti-inflammatory agent, an analgesic agent, a skeletal muscle relaxant, an osteoinductive anabolic growth factor, an anti-catabolic growth factor, an antibiotic or a combination thereof.

6. A flowable composition according to claim 2, wherein the flowable composition further comprises a bolus dose of the therapeutic agent dispersed in the polymer or solvent to provide an immediate release of the therapeutic agent and the effective amount of the therapeutic agent is encapsulated in a plurality of microparticles, microspheres, microcapsules, and/or microfibers to provide sustained release of the therapeutic agent over time.

7. A flowable composition according to claim 1, wherein the hydrophobic polymer segments each consist of poly(D, L-lactic acid), poly(L-lactic acid), or poly(D-lactic acid) and the hydrophilic polymer segments each include polyethylene glycol.

8. A flowable composition according to claim 1, wherein the flowable composition comprises a radiographic marker adapted to assist in radiographic imaging.

9. An implantable drug composition for delivering a therapeutic agent at or near a target tissue site beneath the skin of a patient, the implantable drug comprising a flowable composition comprising an effective amount of a therapeutic agent comprising a corticosteroid from 1 to 30 wt % disposed therein, the flowable composition capable of setting in response to physiological fluid at or near the target tissue site into a substantially non-flowable state, wherein the non-flowable state remains flexible, and wherein the therapeutic agent is released over a period of at least one week, wherein the flowable composition comprises a solvent in an amount of about 15 wt. % of the composition that diffuses away as the flowable composition cures into the substantially non-flowable state, wherein the solvent has a Hildebrand Solubility Parameter of at least about 7.5 or 8 $(cal/cc)^{1/2}$, wherein the flowable composition comprises a polymer, the polymer comprising repeating hydrophobic-hydrophilic polymer segments, wherein the hydrophobic polymer segments are selected from a group consisting of poly(D,L-lactic acid), poly(L-lactic acid), poly(D-lactic acid), poly(γ-butyrolactone), poly(ε-caprolactone-co-lactic acid), poly(c-caprolactone-co-glycolic acid-co-lactic acid), hydroxybutyric acid, malic acid and poly(ethylene carbonate), and wherein the flowable composition comprises a modulus of elasticity of $2\times10^4$ to about $5\times10^5$ dynes/cm$^2$, a predosed viscosity in the range of about 1 to about 200 cps and an inherent viscosity from about 0.10 dL/g to about 1.2 dL/g.

10. An implantable drug composition according to claim 9, wherein the flowable composition is a liquid at room temperature and cures at physiological temperature into the substantially non-flowable state.

11. A kit for implanting a drug at or near a target tissue site beneath the skin of a patient, the kit comprising a flowable composition comprising an effective amount of a drug comprising a corticosteroid from 1 to 30 wt %, the flowable composition capable of setting into a substantially non-flowable state when injected at or near a target tissue site, wherein the flowable composition comprises a solvent in an amount of about 15 wt. % of the composition that diffuses away as the flowable composition sets to form the substantially non-flowable composition, wherein the solvent has a Hildebrand Solubility Parameter of at least about 7.5 or 8 $(cal/cc)^{1/2}$, wherein the flowable composition comprises a polymer, the polymer comprising repeating hydrophobic-hydrophilic polymer segments, wherein the hydrophobic polymer segments consists of one of a group consisting of poly(D,L-lactic acid), poly(L-lactic acid), poly(D-lactic acid), poly(γ-butyrolactone), poly(ε-caprolactone-co-lactic acid), poly(c-caprolactone-co-glycolic acid-co-lactic acid), hydroxybutyric acid, malic acid and poly(ethylene carbonate), and wherein the flowable composition comprises a modulus of elasticity of $2\times10^4$ to about $5\times10^5$ dynes/cm$^2$, a predosed viscosity in the range of about 1 to about 200 cps and an inherent viscosity from about 0.10 dL/g to about 1.2 d L/g.

12. The kit for implanting a drug according to claim 11, wherein the flowable composition develops a denser surface film to form the substantially non-flowable composition.

13. The kit for implanting a drug according to claim 11, wherein the flowable composition is a liquid at room temperature and increases viscosity at physiological temperature to form the substantially non-flowable composition.

14. The kit for implanting a drug according to claim 11, wherein the drug comprises an anti-inflammatory agent, an analgesic agent, a skeletal muscle relaxant, an osteoinductive anabolic growth factor, an anti-catabolic growth factor or a combination thereof.

15. The kit for implanting a drug according to claim 11, wherein the drug is encapsulated in a plurality of microparticles, microspheres, or microcapsules suspended in the flowable composition.

16. The kit for implanting a drug according to claim 11, wherein the flowable composition further comprises a radioopaque agent.

17. A flowable composition according to claim 1, wherein the flowable composition comprises an emulsifier comprising up to 30 wt. % of the flowable composition.

18. A flowable composition according to claim 1, wherein the hydrophobic polymer segments consist of poly(γ-butyrolactone) and the hydrophilic polymer segments comprise polyethylene glycol.

19. A flowable composition according to claim 1, wherein the hydrophobic polymer segments have an average molecular weight less than 1,000 and the hydrophilic polymer segments have an average molecular weight between 300 and 20,000.

20. A flowable composition according to claim 1, wherein the hydrophobic polymer segments have an average molecular weight from about 1,000 to about 3,000 and the hydrophilic polymer segments have an average molecular weight between 500 and 10,000.

* * * * *

UNITED STATES PATENT AND TRADEMARK OFFICE
CERTIFICATE OF CORRECTION

Page 1 of 2

PATENT NO. : 9,504,698 B2
APPLICATION NO. : 12/608300
DATED : November 29, 2016
INVENTOR(S) : Drapeau It is certified that error appears in the above-identified patent and that said Letters Patent is hereby corrected as shown below:

In the Specification

In Column 7, Line 17, delete "ISIS104838," and insert -- ISIS 104838, --, therefor.

In Column 7, Line 46, delete "UO126," and insert -- U0126, --, therefor.

In Column 7, Line 47, delete "Semipimod" and insert -- Semapimod --, therefor.

In Column 8, Lines 34-36, delete "[2-hydroxy-5-[-4-[C2-pyridinylamino)sulfonyl]azo]benzoic acid]," and insert -- [2-hydroxy-5-[[4-[(2-pyridinylamino)sulfonyl]phenyl]azo]benzoic acid], --, therefor.

In Column 9, Line 5, delete "bupivicaine," and insert -- bupivacaine, --, therefor.

In Column 10, Lines 9-10, delete "polyphosphagenes," and insert -- polyphosphazenes, --, therefor.

In Column 12, Lines 1-2, delete "N-methylpyrrolidone" and insert -- N-methyl pyrrolidone --, therefor.

In Column 12, Line 48, delete "poly(c-caprolactone-co-glycolic" and insert -- poly(ε-caprolactone-co-glycolic --, therefor.

In Column 13, Lines 12-13, delete "polyphosphagenes," and insert -- polyphosphazenes, --, therefor.

In the Claims

In Column 18, Line 67, in Claim 1, delete "poly(c-caprolactone-co" and insert -- poly(ε-caprolactone-co --, therefor.

Signed and Sealed this
Twenty-eighth Day of March, 2017

Michelle K. Lee
*Director of the United States Patent and Trademark Office*

CERTIFICATE OF CORRECTION (continued)
U.S. Pat. No. 9,504,698 B2

In Column 20, Line 5, in Claim 9, delete "poly(c-caprolactone-co-glycolic" and insert -- poly(ε-caprolactone-co-glycolic --, therefor.

In Column 20, Line 33, in Claim 11, delete "poly(c-caprolactone-co-glycolic" and insert -- poly(ε-caprolactone-co-glycolic --, therefor.

In Column 20, Line 39, in Claim 11, delete "d L/g." and insert -- dL/g. --, therefor.